(12) United States Patent
Hirama et al.

(10) Patent No.: US 8,299,064 B2
(45) Date of Patent: *Oct. 30, 2012

(54) FUSED POLYCYCLIC COMPOUNDS HAVING A HETEROCYCLIC RING(S) AND PHARMACEUTICAL USE THEREOF

(75) Inventors: Ryusuke Hirama, Kawasaki (JP); Seiji Niwa, Kawasaki (JP); Hideyuki Tanaka, Kawasaki (JP); Toshihiro Hatanaka, Kawasaki (JP); Yoko Masuzawa, Kawasaki (JP); Akiyo Yamazaki, Kawasaki (JP); Takao Ikenoue, Kawasaki (JP); Nobuo Kondo, Kawasaki (JP); Wataru Miyanaga, Kawasaki (JP); Masaru Takayanagi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/040,882

(22) Filed: Mar. 4, 2011

(65) Prior Publication Data

US 2011/0160191 A1    Jun. 30, 2011

Related U.S. Application Data

(60) Division of application No. 11/414,499, filed on May 1, 2006, now Pat. No. 7,928,101, which is a continuation of application No. PCT/JP2004/016217, filed on Nov. 1, 2004.

(30) Foreign Application Priority Data

Oct. 31, 2003   (JP) ................................. 2003-373270

(51) Int. Cl.
| | |
|---|---|
| *A61P 3/10* | (2006.01) |
| *A61P 3/04* | (2006.01) |
| *A61P 9/00* | (2006.01) |
| *A61P 13/12* | (2006.01) |
| *A61P 25/02* | (2006.01) |
| *A61P 27/02* | (2006.01) |
| *A61K 31/5517* | (2006.01) |
| *C07D 487/04* | (2006.01) |

(52) U.S. Cl. ....................................... 514/220; 540/557
(58) Field of Classification Search .................. 514/220; 540/557

See application file for complete search history.

(56) References Cited

U.S. PATENT DOCUMENTS

| | | | |
|---|---|---|---|
| 7,153,850 B2 * | 12/2006 | Iino et al. ...................... | 514/220 |
| 7,326,701 B2 * | 2/2008 | Iino et al. ...................... | 514/220 |
| 7,632,830 B2 | 12/2009 | Iino et al. | |
| 7,807,663 B2 | 10/2010 | Ikenoue et al. | |
| 7,834,006 B2 | 11/2010 | Hirama et al. | |
| 2004/0048847 A1 | 3/2004 | Iino et al. | |
| 2005/0272641 A1 | 12/2005 | Ikenoue et al. | |
| 2008/0108604 A1 | 5/2008 | Tanaka et al. | |

FOREIGN PATENT DOCUMENTS

| | | |
|---|---|---|
| EP | 1 346 993 A1 | 9/2003 |
| JP | 2004-10523 | 1/2004 |
| WO | WO 02/44180 A1 | 6/2002 |
| WO | WO 2004/069259 A1 | 8/2004 |
| WO | WO 2005/068467 A1 | 7/2005 |

OTHER PUBLICATIONS

Keizo Matsuo, et al., "Synthesis of the Novel Furo[3,4-b][1,5]benzodiazepinone and Pyrrolo [3,4-b][1,5]benzodiazepinone Systems[1]", Chemical & Pharmaceutical Bulletin, vol. 32, No. 9, 1984, pp. 3724-3729, XP002577154.

Japanese Office Action mailed Nov. 22, 2010 in Japanese Patent Application No. 2005-515193.

* cited by examiner

*Primary Examiner* — Brenda Coleman
(74) *Attorney, Agent, or Firm* — Oblon, Spivak, McClelland, Maier & Neustadt, L.L.P.

(57) ABSTRACT

The present invention provides a fused polycyclic compound of the following formula, analogues thereof and pharmaceutically acceptable salts thereof; and agents for increasing the sugar-transporting capacity, hypoglycemic agents and pharmaceutical compositions containing the above compounds. This fused polycyclic compound has high medicinal properties and few side-effects, and a therapeutic effect on diabetes.

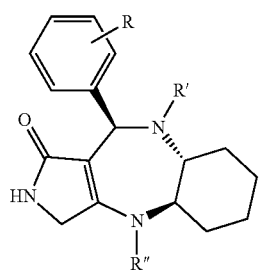

wherein R represents an alkoxy group, R' represents an oxazolylpropionyl group or a thiazolylpropionyl group, and R" represent a hydrogen atom.

20 Claims, No Drawings

FUSED POLYCYCLIC COMPOUNDS HAVING A HETEROCYCLIC RING(S) AND PHARMACEUTICAL USE THEREOF

CROSS-REFERENCE TO RELATED APPLICATIONS

The present application is a divisional of U.S. Ser. No. 11/414,499, filed on May 1, 2006, which is a continuation of PCT/JP04/16217, filed on Nov. 1, 2004, which claims priority to JP 2003-373270, filed on Oct. 31, 2003.

TECHNICAL FIELD OF THE INVENTION

The present invention relates to new fused polycyclic compounds and drugs for treating diabetes which have the compounds as an active ingredient.

BACKGROUND OF THE INVENTION

Drug therapy of Type II diabetes is positioned as a treatment for patients whose conditions are not sufficiently improved by dietary therapy or exercise therapy. Up to now, agents have been developed such as preparations with insulin that is an endogenous hormone controlling hypoglycemic actions, or oral hypoglycemic agents having actions such as insulin secretagogue action or peripheral insulin sensitizing action. At present, it is the mainstream method of drug therapy of Type II diabetes that blood glucose is precisely controlled by using oral hypoglycemic agents. However, in case that sufficient insulin actions cannot be obtained to improve hyperglycemia by using such agents, insulin therapy is applied as a main method. On the other hand, to Type I diabetes, administration of insulin therapy is the only treatment because such patients' insulin secretion ability is extinct.

Thus, though the insulin therapy is used as an important treatment method, there are problems such as procedure complication and need of patient education because it is injection solutions. Accordingly, improvement in the administration method is strongly desired from the aspect of improvement in compliance. Recent years, several insulin administration methods by various non-injection preparations to replace injection solutions have been developed and tried, but they are not led to practical use because of the problems such as the poor absorption efficiency and unstable absorption thereof.

As one of the main hypoglycemic actions of insulin, insulin has the action which increases the sugar-transporting capacity of peripheral cells, makes sugars in the blood take in the peripheral cells, and, as a result, lowers the blood glucose level. Thus, if new oral medicaments are found such as those lowering the blood glucose level by an effect of increasing the sugar-transporting capacity of peripheral cells, it is expected to become a promising treatment for diabetic diseases. For example, the compounds described in Patent Literature 1 are known.

[Patent Literature 1] WO 02/44180

DISCLOSURE OF THE INVENTION

The object of the present invention is to develop and provide a drug for treating diabetes which has high medicinal properties and few side-effects.

The further object of the present invention is to provide an agent having an effect of increasing the sugar-transporting capacity.

The additional object of the present invention is to provide a hypoglycemic agent.

The further additional object of the present invention is to provide a drug for preventing and/or treating diabetes, diabetic peripheral neuropathy, diabetic nephropathy, diabetic retinopathy, diabetic macroangiopathy, impaired glucose tolerance or obesity.

The further additional object of the present invention is to provide a new fused polycyclic compound having a heterocyclic ring(s).

The further additional object of the present invention is to provide a pharmaceutical composition.

The inventors thoroughly examined compounds useful as drugs for treating diabetes, which have a strong effect of increasing the sugar-transporting capacity, and found that specific fused polycyclic compounds have such effects. The present invention has been completed based of this finding.

Namely, the present invention provides the following inventions.

(1) A fused polycyclic compound of the following formula (I) or pharmaceutically acceptable salts thereof:

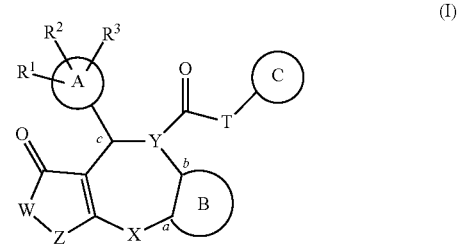

wherein A represents an aromatic cyclic group, a heterocyclic group or an aliphatic cyclic group; B represents an aromatic ring which may have a substituent(s), a heterocyclic ring which may have a substituent(s) or an aliphatic ring which may have a substituent(s); C represents a heterocyclic group which may have a substituent(s); T represents an alkylene group having 1 to 7 carbon atoms which may have a substituent(s) wherein two carbon atoms in the group may have a double bond or triple bond, and a part of carbon atoms in the group may be substituted with —O—, —S—, or —NH—; $R^1$, $R^2$ and $R^3$ may be same or different from each other and each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, a trifluoromethyl group, an alkenyl group which may have a substituent(s), an alkynyl group which may have a substituent(s), an aryl group which may have a substituent(s), a heteroaryl group which may have a substituent(s), a benzyloxy group which may have a substituent(s), an aryloxy group which may have a substituent(s), a heteroaryloxy group which may have a substituent(s), an arylamino group which may have a substituent(s), an arylvinyl group which may have a substituent(s) or an arylethynyl group which may have a substituent(s); —X— and —Z— may be same or different from each other and each independently represent —O—, —NH—, —NR$^6$—, —S—, —SO—, —SO$_2$—, —CH$_2$—, —CR$^4$R$^5$— or —CO—, wherein R$^6$ represents a lower alkyl group which may have a substituent(s), an acyl group which may have a substituent(s), an alkoxycarbonyl group which may have a substituent(s), a carbamoyl group which may have a substituent(s) or a sulfonyl group which may have a substituent(s), $R^4$ and $R^5$ may be same or different from each other and each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group or a trifluoromethyl group; —W— represents —$NR^9$—, —O— or —$CR^7R^8$—, wherein $R^9$ represents a hydrogen atom, a lower alkyl group which may have a substituent(s) or an aryl group which may have a substituent(s), $R^7$ and $R^8$ may be same or different from each other and each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group or a trifluoromethyl group; —Y— represents a nitrogen atom or —CH—; and a, b and c represents a position of a carbon atom, respectively; with the proviso that i) the above substituent(s) is selected from the group consisting of a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, a trifluoromethyl group, an aryl group and a heteroaryl group; and ii) when X is —$CH_2$— or —$CR^4R^5$—, Y is a nitrogen atom.

(2) The fused polycyclic compound or pharmaceutically acceptable salts thereof according to above (1), wherein B is an aliphatic ring which may have a substituent(s); C is a heterocyclic group which may have a substituent(s); —X— is —NH— or —$NR^6$—, —Y— is a nitrogen atom; —Z— is —$CH_2$— or —$CR^4R^5$—; —W— is —$NR^9$—; and -T- is —$CR^{11}R^{12}$—, —$CR^{13}R^{14}$—$CR^{15}R^{16}$— or —$CR^{17}$=$CR^{18}$—, wherein $R^{11}$ to $R^{18}$ each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group.

(3) The fused polycyclic compound or pharmaceutically acceptable salts thereof according to above (2), wherein the heterocyclic group which may have a substituent(s) represented by C is a heteroaryl group which may have a substituent(s).

(4) The fused polycyclic compound or pharmaceutically acceptable salts thereof according to above (2), wherein A is a phenyl group; and the heteroaryl group represented by C is a furyl group which may have a substituent(s), a thienyl group which may have a substituent(s), an oxazolyl group which may have a substituent(s), an isoxazolyl group which may have a substituent(s), a thiazolyl group which may have a substituent(s), an oxadiazolyl group which may have a substituent(s), a thiadiazolyl group which may have a substituent(s), a pyridyl group which may have a substituent(s), a pyridonyl group which may have a substituent(s), a pyridazinyl group which may have a substituent(s), a pyrimidinyl group which may have a substituent(s), an imidazolyl group which may have a substituent(s), or 4-oxothiazolidine-2-thionyl group which may have a substituent(s).

(5) The fused polycyclic compound or pharmaceutically acceptable salts thereof according to above (4), wherein B is a cyclohexane ring which may have a substituent(s).

(6) The fused polycyclic compound or pharmaceutically acceptable salts thereof according to above (5), wherein, in the formula (I), —X— is —NH— or —NMe-; —Y— is a nitrogen atom; —Z— is —$CH_2$—; —W— is —NH—; A is a benzene ring; B is a cyclohexane ring which may have a substituent(s); C is an oxazolyl group which may have a substituent(s), a thiazolyl group which may have a substituent(s), or a pyridinyl group which may have a substituent(s); and -T- is —$CR^{11}R^{12}$—, —$CR^{13}R^{14}$—$CR^{15}R^{16}$— or —$CR^{17}$=$CR^{18}$—, wherein $R^{11}$ to $R^{18}$ each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group.

(7) The fused polycyclic compound or pharmaceutically acceptable salts thereof according to above (2), wherein, in the formula (I), —X— is —NH— or —NMe-; —Y— is a nitrogen atom; —Z— is —$CH_2$— or —$CR^4R^5$—; —W— is —NH—; A is a heterocyclic group; B is a cyclohexane ring which may have a substituent(s); C is an oxazolyl group which may have a substituent(s), a thiazolyl group which may have a substituent(s), or a pyridinyl group which may have a substituent(s); and -T- is —$CR^{11}R^{12}$—, —$CR^{13}R^{14}$—$CR^{15}R^{16}$— or —$CR^{17}$=$CR^{18}$—, wherein $R^{11}$ to $R^{18}$ each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group.

(8) The fused polycyclic compound or pharmaceutically acceptable salts thereof according to above (7), wherein, in the formula (I), —Z— is —$CH_2$—; and A is a heteroaryl group.

(9) The fused polycyclic compound or pharmaceutically acceptable salts thereof according to above (6), wherein at least one of $R^1$, $R^2$, and $R^3$ is —H, —F, -Me, —OMe, —OEt, —SMe, or —$OCF_3$, and the rest(s) is —H.

(10) The fused polycyclic compound or pharmaceutically acceptable salts thereof according to any one of above (6) to (8), wherein the absolute configurations of carbon atoms in a, b, and c of the formula (I) are each independently R or S.

(11) The fused polycyclic compound or pharmaceutically acceptable salts thereof according to above (10), wherein the absolute configurations of carbon atoms in a and b of the formula (I) are R together, and that of a carbon atom in c is R or S.

(12) The fused polycyclic compound or pharmaceutically acceptable salts thereof according to above (10), wherein the absolute configurations of carbon atoms in a and b of the formula (I) are S together, and that of a carbon atom in c is R or S. Further, the present invention provides the following inventions.

(13) An agent for increasing the sugar-transporting capacity, which comprises the fused polycyclic compound or pharmaceutically acceptable salts thereof according to above (1) as an active ingredient.

(14) A hypoglycemic agent; an agent for preventing and/or treating diabetes, diabetic peripheral neuropathy, diabetic nephropathy, diabetic retinopathy, diabetic macroangiopathy, impaired glucose tolerance, or obesity; or a pharmaceutical composition comprising the fused polycyclic compound or pharmaceutically acceptable salts thereof according to above (1) as an active ingredient.

BEST MODE FOR CARRYING OUT THE INVENTION

The reinforcing effect of the sugar transportation in the present invention indicates the action which increases the sugar-transporting capacity via biological membranes. It may act on the sugar transportation from outside to inside of the biological membranes or that from inside to outside of the biological membranes. More concretely, for example, there is an insulin action, that is, the effect of increasing the glucose-transporting in and to adipose cells and muscle cells.

Sugars in the sugar transportation indicates pentoses or hexoses exist in vivo. Examples thereof include glucose, mannose, arabinose, galactose, and fructose. Glucose is preferable among them.

A lower alkyl group represents a linear- or branched-chain or cyclic alkyl group having 1 to 6 carbon atoms. For example, it includes a methyl group, ethyl group, n-propyl group, n-butyl group, n-pentyl group, n-hexyl group, an iso-propyl group, isobutyl group, sec-butyl group, tert-butyl group, isopentyl group, tert-pentyl group, neopentyl group, 2-pentyl group, 3-pentyl group, n-hexyl group, 2-hexyl group, cyclopropyl group, cyclobutyl group, cyclopentyl group and cyclohexyl group. A methyl group and ethyl group are preferable among them.

An aryl group represents a mono- or bi-cyclic aromatic substituent(s) composed of 5 to 12 carbon atoms. Examples thereof are a phenyl group, indenyl group, naphthyl group and fluorenyl group, and a phenyl group is preferable among them.

A halogen atom includes a fluorine atom, chlorine atom, bromine atom and iodine atom.

An alkyl group represents a linear- or branched-chain or cyclic alkyl group having 1 to 18 carbon atoms. For example, it includes a methyl group, ethyl group, n-propyl group, n-butyl group, n-pentyl group, n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, tert-octyl group, cyclopropyl group, cyclobutyl group, cyclopentyl group, cyclohexyl group and 1-adamantyl group. An n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, tert-octyl group, cyclopropyl group, cyclobutyl group, cyclopentyl group, cyclohexyl group, 1-adamantyl group and the like are preferable, and an isopropyl group, tert-butyl group, tert-octyl group, 1-adamantyl group and the like are more preferable among them.

An alkoxy group represents an alkoxy group which has a linear- or branched-chain or cyclic alkyl group having 1 to 18 carbon atoms. For example, it includes a methoxy group, ethoxy group, n-propoxy group, n-butoxy group, n-pentyloxy group, n-hexyloxy group, n-heptyloxy group, n-octyloxy group, n-nonyloxy group, n-decyloxy group, n-undecyloxy group, n-dodecyloxy group, isopropoxy group, isobutoxy group, sec-butoxy group, tert-butoxy group, cyclopropyloxy group, cyclobutoxy group, cyclopentyloxy group, cyclohexyloxy group, cycloheptyloxy group, 2-cyclohexylethoxy group, 1-adamantyloxy group, 2-adamantyloxy group, 1-adamantylmethyloxy group, 2-(1-adamantyl)ethyloxy group and trifluoromethoxy group. Among them, a methoxy group, ethoxy group, n-propoxy group, isopropoxy group, n-butoxy group, tert-butoxy group, n-pentyloxy group and n-hexyloxy group are preferable.

An alkylthio group represents an alkylthio group which has a linear- or branched-chain or cyclic alkyl group having 1 to 12 carbon atoms. For example, it includes a methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group and cyclobutylthio group.

An alkylsulfonyl group represents an alkylsulfonyl group which has a linear- or branched-chain or cyclic alkyl group having 1 to 12 carbon atoms. For example, it includes a methanesulfonyl group, ethanesulfonyl group, propanesulfonyl group, butanesulfonyl group, pentanesulfonyl group, hexanesulfonyl group, heptanesulfonyl group, octanesulfonyl group, nonanesulfonyl group, decanesulfonyl group, undecanesulfonyl group and dodecanesulfonyl group.

An acyl group represents a formyl group, an acyl group which has a linear or branched-chain or cyclic alkyl group having 1 to 6 carbon atoms, an acyl group which has a linear- or branched-chain or cyclic alkenyl group having 1 to 6 carbon atoms, an acyl group which has a linear- or branched-chain or cyclic alkynyl group having 1 to 6 carbon atoms, or an acyl group which has an aryl group that may be substituted. Examples thereof are a formyl group, acetyl group, propionyl group, butyryl group, isobutyryl group, valeryl group, isovaleryl group, pivaloyl group, hexanoyl group, acryloyl group, metacryloyl group, crotonoyl group, isocrotonoyl group, benzoyl group and naphthoyl group.

An acyloxy group represents a formyloxy group, an acyloxy group which has a linear- or branched-chain or cyclic alkyl group having 1 to 6 carbon atoms, or an acyloxy group which has an aryl group that may be substituted. For example, it includes a formyloxy group, acetyloxy group, propionyloxy group, butyryloxy group, isobutyryloxy group, valeryloxy group, isovaleryloxy group, pivaloyloxy group, hexanoyloxy group, acryloyloxy group, metacryloyloxy group, crotonoyloxy group, isocrotonoyloxy group, benzoyloxy group and naphthoyloxy group.

An alkylamino group represents an amino group which is monosubstituted or disubstituted with an alkyl group(s), and examples of the alkyl group(s) are the same as those mentioned in the above "alkyl group." Concretely, they include a methylamino group, ethylamino group, propylamino group, isopropylamino group, dimethylamino group, diethylamino group, dipropylamino group, diisopropylamino group and methylethylamino group.

An alkoxycarbonyl group represents an alkoxycarbonyl group which has a linear- or branched-chain or cyclic alkyl group having 1 to 8 carbon atoms. Examples thereof are a methoxycarbonyl group, ethoxycarbonyl group, propoxycarbonyl group, isopropoxycarbonyl group, n-butoxycarbonyl group, isobutoxycarbonyl group, sec-butoxycarbonyl group, tert-butoxycarbonyl group and benzyloxycarbonyl group.

A carbamoyl group represents a carbamoyl group which may have a linear- or branched-chain or cyclic alkyl group having 1 to 6 carbon atoms on a nitrogen. For example, it includes a carbamoyl group, N-methylcarbamoyl group, N-ethylcarbamoyl group, N,N-dimethylcarbamoyl group, N-pyrrolidylcarbonyl group, N-piperidylcarbonyl group and N-morpholinylcarbonyl group.

A sulfonyl group represents a sulfonyl group which may have a linear- or branched-chain or cyclic alkyl group having 1 to 6 carbon atoms on a sulfur atom. For example, it includes a methylsulfonyl group, ethylsulfonyl group, propylsulfonyl group and butylsulfonyl group.

An aromatic ring represents a monocyclic or bicyclic aromatic ring which is composed of carbon atoms. For example, it includes a benzene ring, naphthalene ring, indene ring and fluorene ring, and a benzene ring and naphthalene ring are preferable.

A heterocyclic ring represents a heterocyclic ring consisting of 1 to 3 ring(s) each comprising 5 to 7 members of carbon and nitrogen, oxygen, sulfur or the like. For example, it includes a pyridine ring, dihydropyran ring, pyridazine ring, pyrimidine ring, pyrazine ring, pyrrole ring, furan ring, thiophene ring, oxazole ring, isooxazole ring, pyrazole ring, imidazole ring, thiazole ring, isothiazole ring, thiadiazole ring, pyrrolidine ring, piperidine ring, piperazine ring, indole ring, isoindole ring, benzofuran ring, isobenzofuran ring, benzothiophene ring, benzopyrazole ring, benzoimidazole ring, benzooxazole ring, benzothiazole ring, purine ring, pyrazolopyridine ring, quinoline ring, isoquinoline ring, naphthyridine ring, quinazoline ring, benzodiazepine ring, carbazole ring and dibenzofuran ring. A pyridine ring, pyrimidine ring, pyridazine ring, pyrimidine ring, furan ring and thiophene ring are preferable among them.

An aromatic cyclic group represents a monocyclic, bicyclic or tricyclic aromatic hydrocarbon group which has no substituent. For example, it includes a phenyl group, naphthalyl group, anthracenyl group and phenanthrenyl group.

A heterocyclic group represents a heterocyclic substituent composed of 1 to 3 ring(s) each comprising 5 to 8 members, having 1 to 4 hetero atom(s) selected from an oxygen atom(s), a sulfur atom(s) and a nitrogen atom(s) as a cyclic atom(s), having no substituent. Meanwhile, an arbitrary carbon atom(s) that is a cyclic atom may be substituted with an oxo group, and a sulfur atom or a nitrogen atom may be oxidized and form an oxide. Further, it may be fused with a benzene ring, and the heterocyclic group may be bridged or form a spirocycle. For example, it includes a pyridyl group, pyridazinyl group, pyrimidyl group (=pyrimidinyl group), pyrazinyl group, furyl group, thienyl group, pyrrolyl group, isoxazolyl group, oxazolyl group, isothiazolyl group, thiazolyl group, pyrazolyl group, imidazolyl group, oxadiazolyl group, thiadiazolyl group, triazoyl group, tetrazolyl group, benzofuranyl group, benzothienyl group, indolyl group, isoindolyl group, benzoxazolyl group, benzothiazolyl group, benzimidazolyl group, indazolyl group, benzisoxazolyl group, benzisothiazolyl group, benzofurazanyl group, benzothiadiazolyl group, purinyl group, quinolyl group (=quinolinyl group), isoquinolyl group, cynnolinyl group, phtharazinyl group, quinazolinyl group, quinoxalinyl group, pteridinyl group, imidazoxazolyl group, imidazothiazolyl group, imidazoimidazolyl group, dibenzofuranyl group, dibenzothienyl group, carbazolyl group, acridinyl group, pyrrolidinyl group, pyrazolidinyl group, imidazolidinyl group, pyrrolinyl group, pyrazolinyl group, imidazolinyl group, tetrahydrofuranyl group, tetrahydrothiophenyl group, thiazolidinyl group, piperidinyl group (=piperidyl group), piperazinyl group, quinuclidinyl group, tetrahydropyranyl group, morpholinyl group, thiomorpholinyl group, dioxolanyl group, homopiperidinyl group (=homopiperidyl group), homopiperazinyl group, indolinyl group, isoindolinyl group, chromanyl group, isochromanyl group, 8-azabicyclo[3.2.1]octan-3-yl group, 9-azabicyclo[3.3.1]nonan-3-yl group, 3-azabicyclo[3.2.1]octan-6-yl group, 7-azabicyclo[2.2.1]peptane-2-yl group, 2-azatricyclo[3.3.1.1]decan-4-yl group, 1-azabicyclo[2.2.2]octan-2-yl group, 1-azabicyclo[2.2.2]octan-3-yl group, 1-azabicyclo[2.2.2]octan-4-yl group, 3-azaspiro[5.5]undecan-9-yl group, 2-azaspiro[4.5]decan-8-yl group, 2-azaspiro[4.4]nonan-7-yl group, and 8-azaspiro[4.5]decan-2-yl group.

An aliphatic cyclic group represents a nonaromatic hydrocarbon group having 3 to 10 carbon atoms, which has no substituent. For example, it includes a cyclopentyl group, cyclohexyl group, and cycloheptyl group.

An aliphatic ring represents a monocyclic or bicyclic aliphatic ring which is composed of carbon atoms. For example, it includes a cyclopropane ring, cyclobutane ring, cyclopentane ring, cyclohexane ring, cycloheptane ring, cyclooctane ring, decalin ring and norbornane ring, and cylohexane ring is preferable.

An heteroaryl group represents an aromatic heterocyclic group consisting of 1 to 3 ring(s) each comprising 5 to 7 members of carbon and nitrogen, oxygen, sulfur or the like. For example, it includes a pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthyridinyl group and quinazolyl group. A 2-pyridyl group, 3-pyridyl group, 4-pyridyl group and 1-pyrazolyl group are preferable among them.

An aryloxy group is an aryloxy group having an aryl group on an oxygen atom, and examples of the aryl group are the same as those mentioned in the above "aryl group." Concretely, it includes a phenoxy group, 1-naphthyloxy group and 2-naphthyloxy group.

A heteroaryloxy group is a heteroaryloxy group having a heteroaryl group on an oxygen atom, and examples of the heteroaryl group are the same as those mentioned in the above "heteroaryl group." Concretely, it includes a 2-pyridyloxy group, 3-pyridyloxy group, 4-pyridyloxy group and 2-pyrimidinyl group.

An arylamino group is an arylamino group having an aryl group(s) on a nitrogen atom and examples of the aryl group(s) are the same as those mentioned in the above "aryl group." Concretely, it includes a phenylamino group, 1-naphthylamino group and 2-naphthylamino group.

An arylvinyl group is a vinyl group of which the first position or the second position is substituted with an aryl group(s), and examples of the aryl group(s) are the same as those mentioned in the above "aryl group." Concretely, it includes a 1-phenylvinyl group and 2-phenylvinyl group.

An arylethynyl group is an ethynyl group of which the second position is substituted with an aryl group(s), and examples of the aryl group(s) are the same as those mentioned in the above "aryl group." Concretely, it includes a phenylethynyl group.

The term "which may have a substituent(s)" indicates the case in which a group does not have any substituents and the case in which, if a group has a substituent(s), at least one or more thereof are substituted with the substituent(s) mentioned in the above (I). The substituent(s) may be same or different from each other, and the position and number thereof are optional and not particularly limited.

Further, in the present invention, the lactam compound of the formula (I) according to claim 1 or pharmaceutically acceptable salts thereof are preferably those mentioned below.

$R^9$ is preferably a hydrogen atom and a methyl group.

$R^1$, $R^2$ and $R^3$ are preferably a hydrogen atom, a halogen atom, a hydroxyl group, an alkyl group, an alkoxy group, an alkylthio group, an acyl group, an acyloxy group, an amino group, an alkoxycarbonyl group, a carbamoyl group, a nitro group, a cyano group, a trifluoromethyl group, a trifluoromethoxy group, an aryl group which may have a substituent(s), a heteroaryl group which may have a substituent(s), a benzyloxy group, an aryloxy group which may have a substituent(s) or an arylethynyl group which may have a substituent(s). More preferable ones are a hydrogen atom, a halogen atom, a hydroxyl group, a methyl group, an ethyl group, a propyl group, an isopropyl group, a methoxy group, an ethoxy group, a methylthio group, an ethylthio group, n-propoxy group, an isopropoxy group, a trifluoromethyl group and a trifluoromethoxy group.

—X— is preferably —NH—, —NR$^6$— wherein R$^6$ represents a lower alkyl group, —O—, —S— or —CH$_2$—. —NH— or —NMe- is more preferable among them.

—Y— is preferably a nitrogen atom.

—Z— is preferably —NH— or —CR$^4$R$^5$— wherein R$^4$ and R$^5$ may be same or different from each other and each independently represent a hydrogen atom or a lower alkyl group which may have a substituent(s), and —CH$_2$— is more preferable.

—W— is preferably —NH—, —NR$^9$— wherein R$^9$ represents a lower alkyl group, or —CH$_2$—, and —NH— or —NMe- is more preferable.

A is preferably an aromatic cyclic group or a heterocyclic group. A phenyl group, a pyridyl group, a pyrimidinyl group, a thienyl group, a benzothienyl group, an indolyl group, a quinolyl group and a benzothiazolyl group are more preferable among them, and a phenyl group, a thienyl group, a benzothienyl group, an indolyl group, a quinolyl group and a benzothiazolyl group are further more preferable, and a phenyl group is particularly preferable among them.

B is preferably an aromatic ring which may have a substituent(s) or an aliphatic ring which may have a substituent(s). A benzene ring which may have a substituent(s) or a cyclohexane ring which may have a substituent(s) is more preferable among them, and a cyclohexane ring which may have a substituent(s) is further more preferable.

When B is a cyclohexane ring which may have a substituent(s), the absolute position of a carbon atom in a and b is preferably R or S, and R is further more preferable.

C is preferably a furyl group which may have a substituent(s), a thienyl group which may have a substituent(s), an oxazolyl group which may have a substituent(s), an isoxazolyl group which may have a substituent(s), a thiazolyl group which may have a substituent(s), an oxadiazolyl group which may have a substituent(s), a thiadiazolyl group which may have a substituent(s), a pyridinyl group which may have a substituent(s), a pyridonyl group which may have a substituent(s), a pyridazinyl group which may have a substituent(s), a pyrimidinyl group which may have a substituent(s), an imidazolyl group which may have a substituent(s), or 4-oxothiazolidine-2-thionyl group which may have a substituent(s). Particularly, an oxazolyl group which may have a substituent(s), a thiazolyl group which may have a substituent(s), and a pyridinyl group which may have a substituent(s) are more preferable.

T is preferably a bond consisting of one or two atom(s). —CH$_2$—, —CR$^{11}$R$^{12}$—, —CR$^{13}$R$^{14}$—CR$^{15}$R$^{16}$— and —CR$^{17}$=CR$^{18}$— wherein R$^{11}$ to R$^{18}$ each independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group are more preferable, and —CH$_2$—, —CH$_2$—CH$_2$— and —CH=CH— are particularly more preferable among them.

The pharmaceutically acceptable salts include, for example, in the case of the compounds of the present invention, which are sufficiently acidic, ammonium salts thereof, alkali metal salts (such as sodium salts and potassium salts, as preferable examples), alkaline earth metal salts (such as calcium salts and magnesium salts, as preferable examples); as salts of an organic base, for example, dicyclohexylamine salts, benzathine salts, N-methyl-D-glucan salts, hydramine salts, and salts of amino acids such as arginine and lysine. Further, in the case of the compounds of the present invention, which are sufficiently basic, the salts include acid addition salts thereof, such as those with inorganic acids, e. g. hydrochloric acid, sulfuric acid, nitric acid and phosphoric acid; or those with organic acids, e. g. acetic acid, lactic acid, citric acid, tartaric acid, maleic acid, fumaric acid and monomethyl sulfate. In some cases, they may be wet salts or hydrates.

The present invention includes all isomers such as optical isomers and geometric isomers, hydrates, solvates or crystal forms.

The compound of the present invention can be synthesized by using or applying the method described in WO02/44180.

For example, in the compound (I) of the present invention, a compound (IV) wherein X and W are —NH—; Z is —CH$_2$—; Y is a nitrogen atom; A is a benzene ring; and B is a cyclohexane ring can be synthesized as mentioned below in accordance with the method described in WO02/44180, by condensing a compound (II) described in WO02/44180 and a carboxylic acid (III) that can be synthesized by using known methods or applying them.

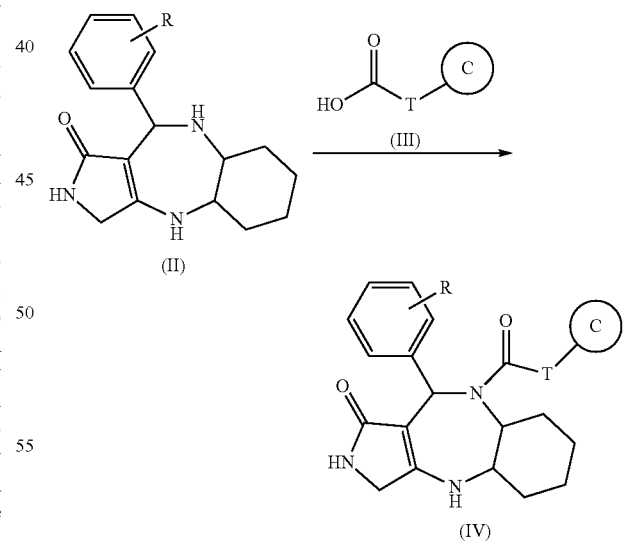

wherein R represents a substituent on a benzene ring.

Further, a compound (VI) wherein, in the above compound (IV), T is —CH$_2$— and C is a thiazole that may have a substituent(s) can be synthesized by leading an ester part of a compound (V) that is obtained by condensation of the compound (II) with a malonic monoester to a thiazole ring in accordance with the publicly known methods.

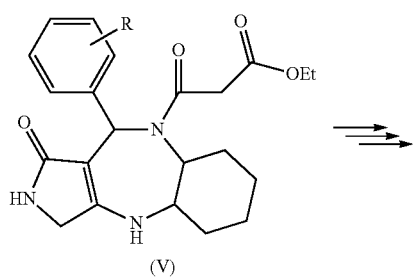

(V)

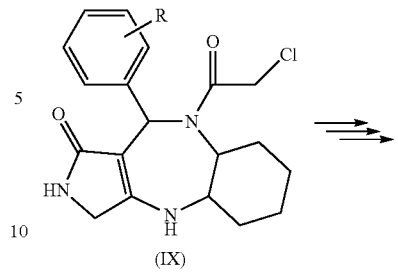

(IX)

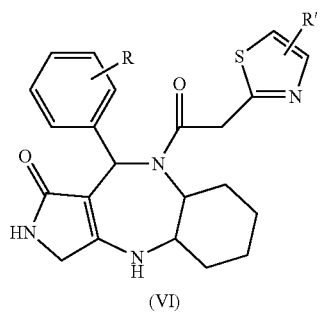

(VI)

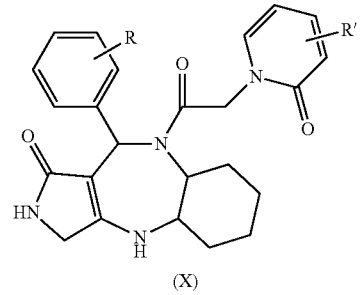

(X)

wherein R represents a substituent on a benzene ring, and R' represents a substituent on a thiazole ring.

Additionally, a compound (VIII) wherein, in the above compound (IV), T is —CH₂—CH₂— and C is an oxadiazole or a thiadiazole that may have a substituent(s) can be synthesized by leading an ester part of a compound (VII) that is obtained by condensation of the compound (II) with a succinic monoester to an oxadiazole ring or a thiadiazole ring in accordance with the publicly known methods.

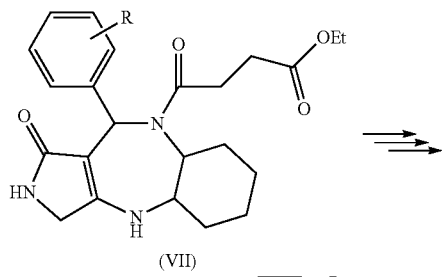

(VII)

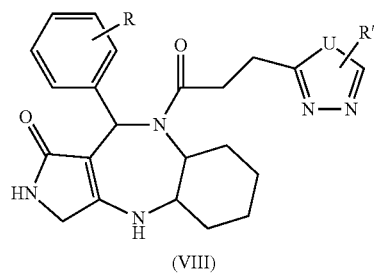

(VIII)

wherein each of R and R' represents a substituent on each rings, and U represents a oxygen atom or a sulfur atom.

Further, a compound (X) wherein, in the above compound (IV), T is —CH₂— and C is a pyridone that may have a substituent(s) can be synthesized by the substitution reaction of a chloro group(s) to a compound (IX) that is obtained by condensation of the compound (II) with a chloroacetic anhydride.

wherein each of R and R' represents a substituent on each rings.

The compounds of the present invention other than those mentioned above can also be synthesized by applying the above reactions.

Meanwhile, the compounds of the present invention obtained by the above methods can be purified with methods usually used in organic syntheses, such as extraction, distillation, crystallization and column chromatography.

The obtained compounds of the present invention have an effect of increasing the sugar-transporting capacity as mentioned below, and are useful for treating patients, taking advantage of this action. Namely, since an effect of increasing the sugar-transporting capacity lowers the blood glucose level, the compounds of the present invention are useful as drugs preventing and/or treating diabetes, diabetic peripheral neuropathy, diabetic nephropathy, diabetic retinopathy, diabetic macroangiopathy, impaired glucose tolerance or obesity.

When using the compounds of the present invention as the drugs preventing and/or treating diabetes, diabetic peripheral neuropathy, diabetic nephropathy, diabetic retinopathy, diabetic macroangiopathy, impaired glucose tolerance or obesity, they can be administered orally, intravenously, or transdermally. Though the dosage differs depending on a patient's symptom, age and administration method, it is usually 0.001 to 1000 mg/kg/day.

The compounds of the present invention can be formulated into a pharmaceutical preparation by ordinary methods. The dosage forms are, for example, injection solvents, tablets, granules, subtle granules, powders, capsules, cream pharmaceuticals and suppositories. The preparation carriers include such as lactose, glucose, D-mannitol, starch, crystalline cellulose, calcium carbonate, kaolin, starch, gelatin, hydroxypropyl cellulose, hydroxypropyl methyl cellulose, polyvinylpyrrolidone, ethanol, carboxy methyl cellulose, carboxy methyl cellulose calcium salts, magnesium stearate, talc, acetyl cellulose, sucrose, titanium oxide, benzoic acid, p-hydroxybenzoate ester, sodium dehydroacetate, gum arabic, tragacanth, methyl cellulose, egg yolk, surfactants, sucrose, simple syrup, citric acid, distilled water, ethanol, glycerin, propylene glycols, macrogol, monobasic sodium phosphate, dibasic sodium phosphate, sodium phosphate, glucose, sodium chloride, phenol, thimerosal, p-hydroxybenzoate ester and acid sodium sulfite. They are used by being mixed with the compounds of the present invention depending on the dosage forms.

Further, the content of the active ingredient of the present invention in the preparation of the present invention significantly varies depending on the dosage forms and is not particularly limited. Generally, the content is about 0.01 to 100 wt %, and preferably 1 to 100 wt % to a total amount of compositions.

The compounds of the present invention have an effect of increasing the sugar-transporting capacity, and are useful for treating the diabetic diseases. Namely, since an effect of increasing the sugar-transporting capacity lowers the blood glucose, the compounds of the present invention are useful as drugs preventing and/or treating diabetes, diabetic peripheral neuropathy, diabetic nephropathy, diabetic retinopathy, diabetic macroangiopathy, impaired glucose tolerance or obesity.

EXAMPLES

Next, Examples will further illustrate the present invention. They only explain the present invention and do not particularly limit the invention.

Examples 1 to 55

The Compounds 1 to 47 described in the following Table 1 and the Compounds 48 to 55 described in Table 1-2 were synthesized in accordance with the method described in WO02/44180.

In this regard, the symbols in Tables are as follows: No.: Example/Compound No., R: a substituent on a benzene ring, R': an acyl group, R": an alkyl group, D: data on the compound, MS:ESI-MS m/z, N1: 1H-NMR (DMSO-d6, TMS internal standard, δ ppm). The number located in front of a substituent in R indicates the position of the substituent on a benzene ring.

TABLE 1

| No. | R | R' | R" | D |
|---|---|---|---|---|
| 1 | 2-OMe | —C(O)CH₂CH₂-(2-thienyl) | H | N1: 0.50-3.40 (13H, m), 3.68 (3H, s), 3.73 (1H, J = 16.0 Hz, d), 3.81 (1H, J = 16.0 Hz, d), 3.94-4.08 (1H, m), 5.80 (1H, s), 6.65 (1H, s), 6.69 (1H, s), 6.83-7.04 (5H, m), 7.24-7.32 (2H, m) MS: 452 (M + H)+ |
| 2 | 2-OMe | —C(O)CH₂CH₂-(2-furyl) | H | N1: 0.50-3.40 (13H, m), 3.74 (1H, J = 16.0 Hz, d), 3.77 (3H, s), 3.82 (1H, J = 16.0 Hz, d), 3.90-4.07 (1H, m), 5.82 (1H, s), 6.04 (1H, J = 3.0 Hz, d), 6.30-6.34 (1H, m), 6.65 (1H, s), 6.70 (1H, s), 6.85-7.04 (3H, m), 7.24-7.32 (1H, m), 7.47-7.51 (1H, m) MS: 436 (M + H)+, 434 (M − H)− |
| 3 | 2-OMe | —C(O)CH₂CH₂-(3-thienyl) | H | N1: 0.51-3.38 (13H, m), 3.55-3.89 (9H, m), 3.72 (3H, s), 3.73-3.88 (2H, m), 3.94-4.08 (1H, m), 5.83 (1H, s), 6.64 (1H, s), 6.68 (1H, s), 6.81-7.46 (7H, m)−. MS: 452 (M + H)+, 450 (M − H)−. |
| 4 | 2-OMe | —C(O)CH₂CH₂-(3-pyridyl) | H | N1: 0.50-3.40 (13H, m), 3.71 (3H, s), 3.73 (1H, J = 16.0 Hz, d), 3.80(1H, J = 16.0 Hz, d), 3.90-4.05 (1H, m), 5.81 (1H, s), 6.65 (1H, s), 6.70 (1H, s), 6.84-7.04 (3H, m), 7.23-7.33 (2H, m), 7.60-7.69 (1H, m), 8.34-8.49 (2H, m) MS: 447 (M + H)+ |
| 5 | 2-OMe | —C(O)CH₂CH₂-(4-pyridyl) | H | N1: 0.50-3.61 (13H, m), 3.65-4.07 (3H, m), 3.73 (3H, s), 5.82 (1H, s), 6.65 (1H, s), 6.71 (1H, s), 6.61-8.48 (8H, m)−. MS: 447 (M + H)+, 445 (M − H)−. |

TABLE 1-continued

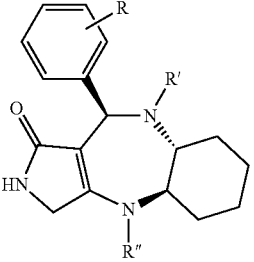

| No. | R | R' | R'' | D |
|---|---|---|---|---|
| 6 | 2-Me | 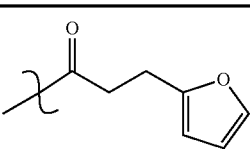 | H | N1: 0.50-3.40 (13H, m), 2.33 (3H, s), 3.76 (1H, J = 16.0 Hz, d), 3.86 (1H, J = 16.0 Hz, d), 3.90-4.03 (1H, m), 5.67 (1H, s), 5.98-6.04 (1H, m), 6.28-6.34 (1H, m), 6.71 (1H, s), 6.78 (1H, s), 7.00-7.24 (4H, m), 7.45-7.50 (1H, m) MS: 420 (M + H)+, 418 (M − H)− |
| 7 | H | 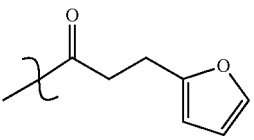 | H | N1: 0.50-3.40 (13H, m), 3.76 (1H, J = 16.0 Hz, d), 3.83 (1H, J = 16.0 Hz, d), 3.92-4.06 (1H, m), 5.70 (1H, s), 6.04-6.09 (1H, s), 6.30-6.36 (1H, m), 6.71 (1H, s), 6.78 (1H, s), 7.20-7.39 (4H, m), 7.46-7.51 (1H, m) MS: 405 (M + H)+, 404 (M − H)− |
| 8 | 2-F | 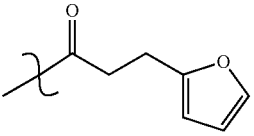 | H | N1: 0.50-3.40 (13H, m), 3.78 (1H, J = 16.0 Hz, d), 3.85 (1H, J = 16.0 Hz, d), 3.93-4.07 (1H, m), 5.86 (1H, s), 6.02-6.07 (1H, m), 6.29-6.35 (1H, m), 6.76-6.85 (2H, m), 7.07-7.50 (5H, m) MS: 424 (M + H)+, 422 (M − H)− |
| 9 | 2-Me | 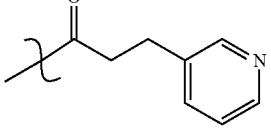 | H | N1: 0.50-3.40 (13H, m), 2.28 (3H, s), 3.72 (1H, J = 16.0 Hz, d), 3.83 (1H, J = 16.0 Hz, d), 3.87-4.03 (1H, m), 5.68 (1H, s), 6.68 (1H, s), 6.75 (1H, s), 6.97-7.30 (5H, m), 7.58-7.66 (1H, m), 8.34-8.46 (2H, m) MS: 431 (M + H)+, 429 (M − H)− |
| 10 | 2-OMe | 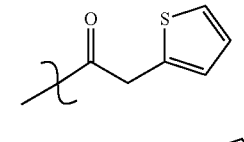 | H | N1: 0.50-2.95 (9H, m), 3.62 (1H, d, J = 15.9 Hz), 3.75 (1H, d, J = 15.9 Hz), 3.83 (3H, s), 3.95-4.05 (1H, m), 4.07 (1H, d, J = 16.2 Hz), 4.14 (1H, d, J = 16.2 Hz), 5.90 (1H, s), 6.60 (1H, s), 6.64 (1H, s), ( 6.85-7.35 (7H, m). MS: 438 (M + H)+, 436 (M − H)−. |
| 11 | 2-OMe | 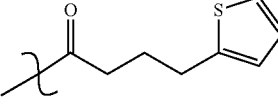 | H | N1: 0.50-2.90 (15H, m), 3.71 (3H, s), 3.74 (1H, d, J = 16.2 Hz), 3.82 (1H, d, J = 16.2 Hz), 3.95-4.05 (1H, m), 5.78 (1H, s), 6.64 (1H, s), 6.70 (1H, s), 6.75-7.34 (4H, m). MS: 464 (M − H)−. |
| 12 | 2-OMe | 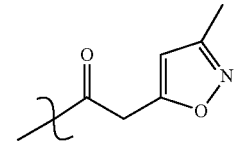 | H | N1: 0.50-2.90 (9H, m), 2.17 (3H, s), 3.70 (1H, d, J = 16.8 Hz), 3.80 (1H, d, J = 16.2 Hz), 3.86 (3H, s), 3.90-4.00 (1H, m), 4.01 (1H, d, J = 16.2 Hz), 4.12 (1H, d, J = 16.8 Hz), 5.76 (1H, s), 6.15 (1H, s), 6.68 (1H, s), 6.72 (1H, s), 6.87-7.40 (4H, m). MS: 435 (M − H)−. |
| 13 | 2-Me | 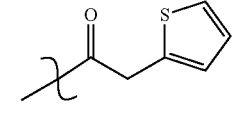 | H | N1: 0.45-2.85 (9H, m), 2.32 (3H, s), 3.62 (1H, d, J = 16.2 Hz), 3.78 (1H, d, J = 16.2 Hz), 3.90-4.05 (1H, m), 5.80 (1H, s), 6.65 (1H, s), 6.71 (1H, s), 6.85-7.35 (7H, m). MS: 422 (M + H)+, 420 (M− H)−. |
| 14 | 2-OMe | 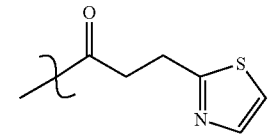 | H | N1: 0.50-3.40 (9H, m), 3.73 (3H, s), 3.70-3.85 (2H, m), 3.90-4.05 (1H, m), 5.81 (1H, s), 6.67 (1H, s), 6.71 (1H, s), 6.86-7.31 (4H, m), 7.53 (1H, d, J = 3.3 Hz), 7.67 (1H, d, J = 3.3 Hz). MS: 453 (M + H)+, 451 (M − H).− |

TABLE 1-continued

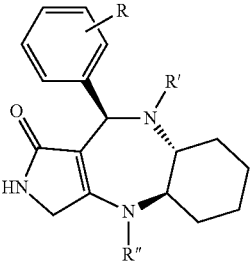

| No. | R | R' | R" | D |
|---|---|---|---|---|
| 15 | 2-OMe | 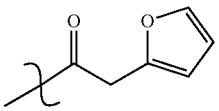 | H | N1: 0.50-2.90 (9H, m), 3.69 (1H, d, J = 16.5 Hz), 3.79 (1H, d, J = 16.5 Hz), 3.85 (3H, s), 3.85-4.00 (2H, m), 3.90-4.00 (2H, m), 5.53 (1H, s), 6.17 (1H, brs), 6.33 (1H, brs), 6.62 (1H, s), 6.68 (1H, s), 6.87-7.32 (4H, m), 7.49 (1H, brs). MS: 422 (M + H)+, 420 (M− H)−. |
| 16 | 2-Me | 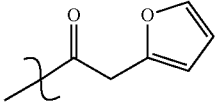 | H | N1: 0.45-2.80 (9H, m), 2.34 (3H, s), 3.72 (1H, d, J = 16.5 Hz), 3.84 (1H, d, J = 16.5 Hz), 3.90-4.05 (1H, m), 5.72 (1H, s), 6.20 (1H, d, J = 3.0 Hz), 6.34 (1H, dd, J = 3.0, 3.0 Hz), 6.68 (1 H, s), 6.75 (1H, s), 7.01-7.25 (4H, m), 7.50-7.51 (1H, m). MS: 404 (M − H)−. |
| 17 | 2-OMe | 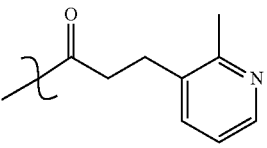 | H | N1: 0.50-3.00 (13H, m), 2.47 (3H, s), 3.74 (3H, s), 3.74 (1H, d, J = 16.21 Hz), 3.82 (1H, d, J = 16.2 Hz), 3.90-4.05 (1H, m), 5.83 (1H, s), 6.66 (1H, s), 6.72 (1H, s), 6.85-7.31 (4H, m), 7.09-8.26 (3H, m). MS: 461 (M + H)+, 459 (M − H)−. |
| 18 | 2-OMe | 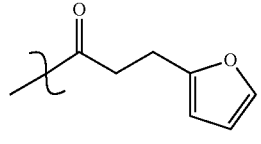 | Me | N1: 0.50-3.40 (13H, m), 2.78 (3H, s), 3.77 (3H, s), 3.82 (1H, J = 16.0 Hz, d), 3.85-3.99 (1H, m), 4.08 (1H, J = 16.0 Hz, d), 5.78 (1H., s), 6.00-6.05 (1H, m), 6.30-6.35 (1H, m), 6.86-7.08 (4H, m), 7.24-7.33 (2H, m), 7.45-7.49 (1H, m) MS: 450 (M + H)+ |
| 19 | 2-Me | 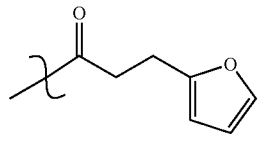 | Me | N1: 0.50-3.40 (13H, m), 2.31 (3H, s), 2.77 (3H, s), 3.83-3.96 (1H, m), 3.87 (1H, J = 16.0 Hz, d), 4.07 (1H, J = 16.0 Hz, d), 5.65 (1H, s), 5.96-6.00 (1H, m), 6.31-6.35 (1H, m), 7.06-7.24 (6H, m), 7.44-7.50 (1H, m) MS: 434 (M + H)+ |
| 20 | 2-OMe | 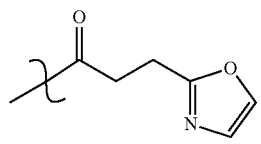 | H | N1: 0.50-3.05 (14H, m), 3.75 (1H, d, J = 16.5 Hz), 3.82 (1H, d, J = 16.5 Hz), 3.83 (3H, s), 3.90-4.05 (1H, m), 5.83 (1H, s), 6.65 (1H, s), 6.72 (1H, s), 6.86-7.32 (4H, m), 7.07 (1H, s), 7.96 (1H, s). MS: 437 (M + H)+, 435 (M − H)−. |
| 21 | 2-Me | 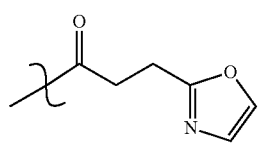 | H | N1: 0.45-3.40 (13H, m), 2.37 (3H, s), 3.77 (1H, d, J = 16.5 Hz), 3.86 (1H, d, J = 16.5 Hz), 3.90-4.00 (1H, m), 5.68 (1H, s), 6.70 (1H, s), 6.78 (1H, s), 7.03-7.21 (4H, m), 7.05 (1H, s), 7.93 (1H, s). MS: 419 (M − H)−. |
| 22 | 2-Me | 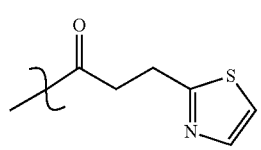 | H | N1: 0.45-3.20 (13H, m), 2.33 (3H, s), 3.75 (1H, d, J = 16.5 Hz), 3.85 (1H, d, J = 16.5 Hz), 3.90-4.05 (1H, m), 5.66 (1H, s), 6.71 (1H, s), 6.77 (1H, s), 7.00-7.24 (4H, m), 7.52 (1H, d, J = 3.3 Hz), 7.66 (1H, d, J = 3.3 Hz). MS: 434 (M − H)−. |

TABLE 1-continued

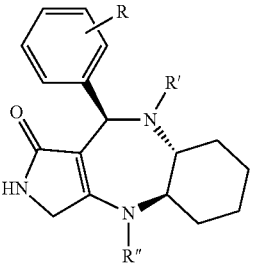

| No. | R | R' | R'' | D |
|---|---|---|---|---|
| 23 | 2-OMe | 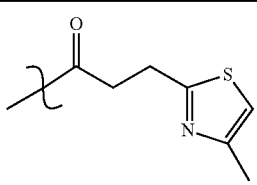 | H | N1: 0.50-3.40 (14H, m), 2.30 (3H, s), 3.7 3(1H, d, J = 16.5 Hz), 3.75 (3H, s), 3.82 (1H, d, J = 16.5 Hz), 3.90-4.05 (1H, m), 5.81 (1H, s), 6.66 (1H, s), 6.71 (1H, s), 6.84-7.38 (4H, m). MS: 467 (M + H)+, 466 (M − H)−. |
| 24 | 2-OMe | 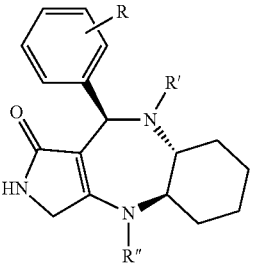 | H | N1: 0.86-3.18 (13H, m), 2.18 (3H, s), 3.80-3.87 (5H, m), 3.99 (1H, s), 6.10 (1H, s), 6.71-7.33 (6H, m). MS: 451 (M + H)+. |
| 25 | 2-Me | 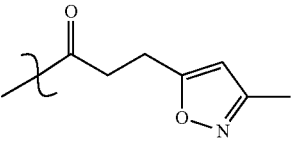 | H | N1: 0.45-3.20 (13H, m), 2.34 (3H, s), 3.76 (1H, d, J = 16.8 Hz), 3.86 (1H, d, J = 16.8 Hz), 3.90-4.05 (1H, m), 5.69 (1H, s), 6.69 (1H, s), 6.76 (1H, s), 7.00-7.26 (4H, m), 7.14-8.46 (4H, m). MS: 431 (M + H)+, 429 (M − H)−. |
| 26 | 2-OMe | 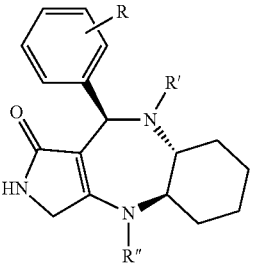 | H | N1: 0.85-3.17 (13H, m), 2.16 (3H, s), 2.29 (3H, s), 3.69-3.84 (5H, m), 5.80 (1H, s), 6.63-7.32 (6H, m). MS: 465 (M + H)+. |
| 27 | 2-OMe | 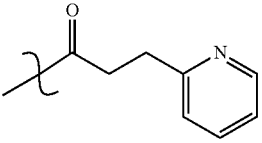 | H | N1: 0.50-3.30 (13H, m), 2.37 (3H, s), 3.73 (1H, d, J = 16.5 Hz), 3.74 (3H, s), 3.82 (1H, d, J = 16.5 Hz), 3.90-4.05 (1H, m), 5.81 (1H, s), 6.66 (1H, s), 6.71 (1H, s), 6.84-7.34 (4H, m), 7.31 (1H, d, J = 1.5 Hz). MS: 465 (M − H)−. |
| 28 | 2-OMe | 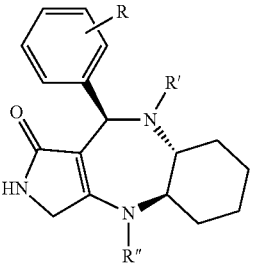 | H | N1: 0.55-3.05 (9H, m), 3.74 (1H, d, J = 16.5 Hz), 3.82 (1H, d, J = 16.5 Hz)( 3.90-4.05 (1H, m), 3.83 (3H, s), 4.05-4.20 (1H, m), 6.01 (1H, s), 6.73 (1H, s), 6.73 (1H, s), 6.86-7.10 (4H, m), 7.50 (1H, d, J = 16.3 Hz), 7.76 (1H, d, J = 15.6 Hz), 7.84 (1H, d, J = 3.0 Hz), 7.94 (1H, d, J = 3.0 Hz). MS: 449 (M − H)−. |
| 29 | 2-Me | 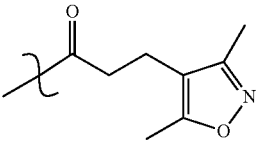 | H | N1: 0.50-3.00 (9H, m), 2.32 (3H, s), 3.78 (1H, d, J = 16.2 Hz), 3.87 (1H, d, J = 16.2 Hz), 4.00-4.15 (1H, m), 5.92 (1H, s), 6.80 (1H, s), 6.80 (1H, s), 7.04-7.25 (4H, m), 7.46 (1H, d, J = 14.4 Hz), 7.61 (1H, d, J = 14.7 Hz), 7.87 (1H, d, J = 3.0 Hz), 7.95 (1H, d, J = 3.3 Hz). MS: 432 (M − H)−. |
| 30 | 2-OMe | 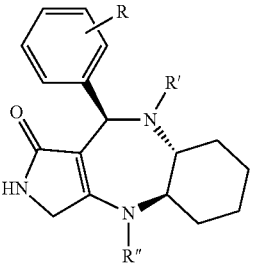 | H | N1: 0.50-3.15 (13H, m), 2.28 (3H, s), 3.75 (1H, d, J = 15.9 Hz), 3.83 (1H, d, J = 16.9 Hz), 3.85-3.95 (1H, m), 3.85 (3H, s), 5.82 (1H, s), 6.67 (1H, s), 6.74 (1H, s), 6.85-7.34 (4H, m). MS: 450 (M − H)−. |

TABLE 1-continued

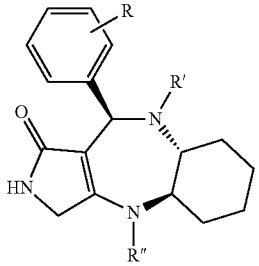

| No. | R | R' | R" | D |
|---|---|---|---|---|
| 31 | 2-Me | 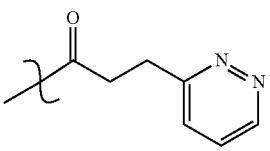 | H | N1: 0.50-3.40 (13H, m), 2.36 (3H, s), 3.65-4.10 (3H, m), 5.71 (1H, brs), 6.70 (1H, brs), 6.78 (1H, brs), 7.00-7.70 (6H, m), 9.06 (1H, s) MS: 432 (M + H)+, 430 (M − H)− |
| 32 | 2-OMe | 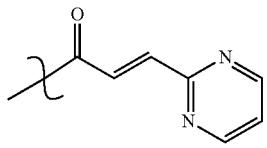 | H | N1: 0.50-3.40 (9H, m), 3.70-3.90 (2H, m), 3.82 (3H, s), 4.10-4.20 (1H, m), 6.09 (1H, s), 6.75 (2H, s), 6.90-7.10 (3H, m), (7.25-7.38 (2H, m), 7.45 (1H, t, J = 4.8 Hz), 8.22 (1H, d, J = 15.0 Hz), 8.87 (2H, d, J = 4.8 Hz) MS: 446 (M + H)+, 444 (M − H)−. |
| 33 | 2-OMe | 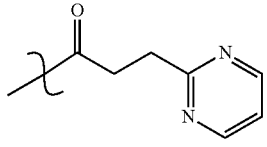 | H | N1: 0.50-3.40 (13H, m), 3.70-3.90 (2H, m), 3.85 (3H, s), 3.90-4.05 (1H, m), 5.90 (1H, s), 6.65 (1H, s), 6.72 (1H, s), 6.88-7.34 (5H, m), 8.72 (2H, d, J = 5.1 Hz) MS: 448 (M + H)+, 446 (M − H)− |
| 34 | 2-OCF3 | 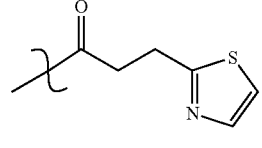 | H | N1: 0.55-3.30 (13H, m), 3.77 (1H, d, J = 16.5 Hz), 3.85 (1H, d, J = 16.5 Hz), 3.95-4.05 (1H, m), 5.84 (1H, s), 6.82 (1H, s), 6.83 (1H, s), 7.20-7.50 (4H, m), 7.52 (1H, d, J = 3.3 Hz), 7.65 (1H, d, J = 3.3 Hz). MS: 505 (M − H)−. |
| 35 | 2-OCF3 | 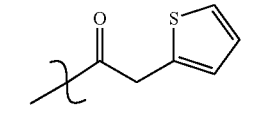 | H | N1: 0.50-3.40 (9H, m), 3.51-3.83 (2H, m), 3.94-4.18 (3H, m), 5.95 (1H, s), 6.74 (1H, s), 6.84-6.93 (2H, m), 7.22-7.55 (5H, m) MS: 490 (M − H)− |
| 36 | 2-OCF3 | 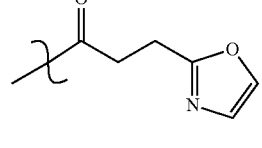 | H | N1: 0.55-3.20 (13H, m), 3.78 (1H, d, J = 16.5 Hz), 3.86 (1H, d, J = 16.5 Hz), 3.90-4.02 (1H, m), 5.86 (1H, s), 6.80 (1H, s), 6.83 (1H, s), 7.20-7.42 (4H, m), 7.93 (1H, s). MS: 489 (M − H)−. |
| 37 | 2-OMe | 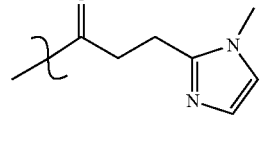 | H | N1 (CD3OD): 0.90-3.26 (13H, m), 3.80-3.98 (5H, m), 4.08 (1H, m), 6.04 (1H, s), 6.90-7.33 (6H, m). MS: 450 (M + H)+. |
| 38 | 2-OMe | 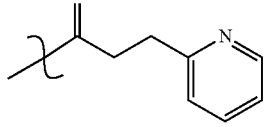 | H | N1: 0.50-3.30 (13H, m), 3 75 (1H, d, J = 16.5 Hz), 3.78 (3H, s), 3.82 (1H, d, J = 16.5 Hz), 3.90-4.05 (1H, m), 5.84 (1H, s), 6.65 (1H, s), 6.70 (1H, s), 6.84-7.22 (4H, m), 7.23-8.50 (4H, m). MS: 445 (M − H)−. |

TABLE 1-continued

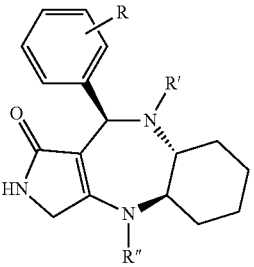

| No. | R | R' | R" | D |
|---|---|---|---|---|
| 39 | 2-Me | 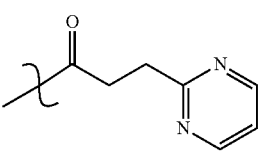 | H | N1: 0.50-3.40 (16H, m), 3.75-4.00 (3H, m), 5.75 (1H, s), 6.70 (1H, s), 6.78 (1H, s), 7.00-7.27 (4H, m), 7.31 (1H, t, J = 5.0 Hz), 8.69 (2H, d, J = 5.0 Hz) MS: 432 (M + H)+, 430 (M − H)−. |
| 40 | 2-OCF3 | 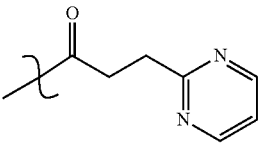 | H | N1: 0.50-3.40 (13H, m), 3.75-4.10 (3H, m), 5.93 (1H, s), 6.81 (1H, s), 6.83 (1H, s), 6.90-7.10 (3H, m), 7.30-7.48 (5H, m), 8.70 (2H, d, J = 5.1 Hz) MS: 502 (M + H)+, 500 (M − H)−. |
| 41 | 2-OEt | 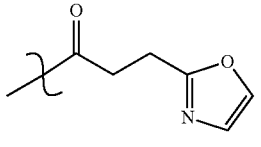 | H | N1: 0.50-3.40 (13H, m), 1.31 (3H, t), 3.73-4.18 (5H, m), 5.84 (1H, s), 6.68 (1H, s), 6.75 (1H, s), 6.89 (1H, t), 7.01 (2H, d), 7.08 (1H, s), 7.26 (1H, t), 7.96 (1H, s) MS: 451 (MH+), 449 (M − H)− |
| 42 | 2-OEt | 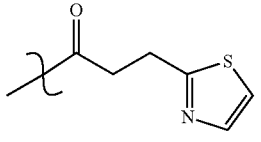 | H | N1: 0.50-3.25 (13H, m), 1.22 (3H, t. J = 6.9 Hz), 3.75 (1H, d, J = 16.2 Hz), 3.82 (1H, d, J = 16.2 Hz), 3.90-4.10 (3H, m), 5.80 (1H, s), 6.67 (1H, s), 6.72 (1H, s), 6.82-7.30 (4H, m), 7.53 (1H, d, J = 3.3 Hz), 7.66 (1H, d, J = 3.3 Hz). MS: 465 (M − H)−. |
| 43 | 2-SMe | 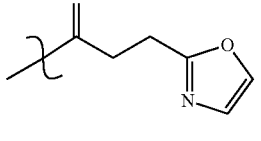 | H | N1: 0.50-3.40 (16H, m), 3.76-4.00 (3H, m), 5.70 (1H, brs), 6.75 (1H, brs), 6.80 (1H, brs), 7.03-7.44 (5H, m), 7.96 (1H, s) MS: 453 (M + H)+, 451(M − H)− |
| 44 | 2-SMe | 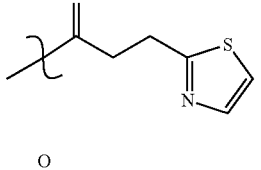 | H | N1: 0.50-3.40 (16H, m), 3.77 (1H, d, J = 16.7 Hz), 3.88 (1H, d, J = 16.7 Hz), 3.96 (1H, m), 5.69 (1H, brs), 6.73 (1H, brs), 6.79 (1H, brs), 7.02-7.42 (4H, m), 7.52-7.68 (2H, m) MS: 469 (M + H)+, 467 (M − H)− |
| 45 | 2-OMe | 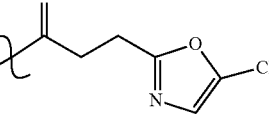 | H | N1: 0.50-3.50 (13H, m), 3.70-4.00 (6H, m), 5.85 (1H, s), 6.67 (1H, s), 6.75 (1H, s), 6.88-7.35 (4H, m), 7.85-7.90 (1H, m) MS: 505 (M + H)+, 503 (M − H)− |
| 46 | 2-OMe | 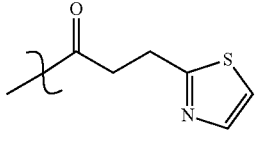 | Me | MS: 467 (M + H)+, N1: 0.45-3.30 (13H, m), 2.77 (3H, s), 3.81 (1H, d, J = 16.5 Hz), 3.85-4.00 (1H, m), 4.05 (1H, d, J = 16.5 Hz), 5.78 (1H, s), 6.85-7.32 (4H, m), 7.03 (1H, s), 7.53 (1H, d, J = 3.3 Hz), 7.65 (1H, d, J = 3.3 Hz). |

TABLE 1-continued
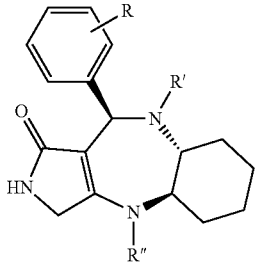
| No. | R | R' | R" | D |
|---|---|---|---|---|
| 47 | 2-OCF₃ | 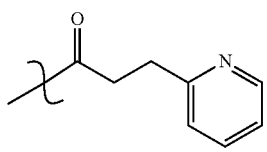 | H | MS: 501 (M + H)+, N1: 0.50 (13H, m), 3.77 (1H, d, J = 16.5 Hz), 3.85 (1H, d, J = 16.5 Hz), 3.95-4.05 (1H, m), 5.87 (1H, s), 6.79 (1H, s), 6.81 (1H, s), 7.14-8.48 (8H, m) |
TABLE 1-2
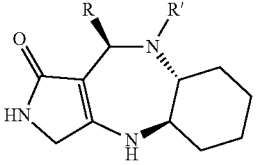
| No. | R | R' | D |
|---|---|---|---|
| 48 | 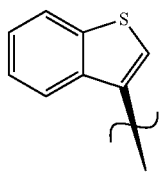 | 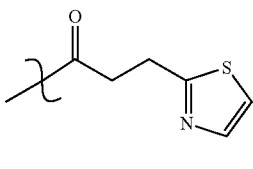 | MS: 479 (M + H)+, N1: 0.35-3.40 (13H, m), 3.76 (1H, d, J = 16.2 Hz), 3.85 (1H, d, J = 16.2 Hz), 3.90-4.05 (1H, m), 5.94 (1H, s), 6.74 (1H, s), 6.81 (1H, s), 7.31 (1H, s), 7.35-7.45 (2H, m), 7.56 (1H, d, J = 3.3 Hz), 7.71 (1H, d, J = 3.3 Hz), 7.80-7.90 (1H, m), 7.94-8.02 (1H, m). |
| 49 | 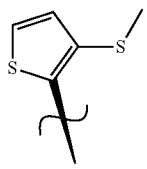 | 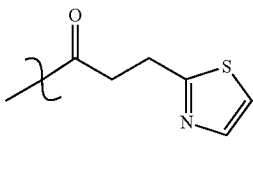 | MS: 475 (M + H)+, N1: 0.60-3.40 (13H, m), 2.43 (3H, s), 3.71 (1H, d, J = 16.5 Hz), 3.77 (1H, d, J = 16.5 Hz), 3.90-4.05 (1H, m), 5.76 (1H, s), 6.78 (1H, s), 6.84 (1H, s), 7.14 (1H, d, J = 5.4 Hz), 7.45 (1H, d, J = 5.4 Hz), 7.52 (1H, d, J = 3.3 Hz), 7.65 (1H, d, J = 3.3 Hz). |
| 50 | 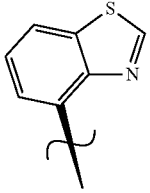 | 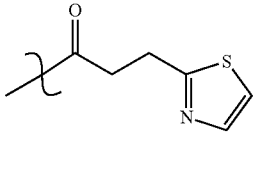 | MS: 480 (M + H)+, N1: 0.40-3.30 (13H, m), 3.81 (1H, d, J = 16.2 Hz), 3.88 (1H, d, J = 16.2 Hz), 3.95-4.10 (1H, m), 6.44 (1H, s), 6.76 (1H, s), 6.79 (1H, s), 7.25 (1H, d, J = 7.2 Hz), 7.45 (1H, dd, J = 7.2, 7.2 Hz), 7.53 (1H, d, J = 3.3 Hz), 7.67 (1H, d, J = 3.3 Hz), 8.12 (1H, d, J = 7.2 Hz), |
| 51 | 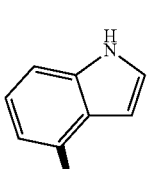 | 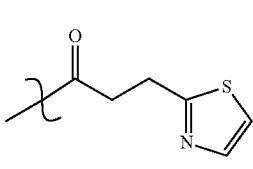 | MS: 462 (M + H)+, N1: 0.30-3.40 (13H, m), 3.76 (1H, d, J = 16.5 Hz), 3.86 (1H, d, J = 16.5 Hz), 3.90-4.04 (1H, m), 5.99 (1H, s), 6.41-7.34 (5H, m), 6.66 (1H, s), 6.74 (1H, s), 7.54 (1H, d, J = 3.3 Hz), 7.69 (1H, d, J = 3.3 Hz), 11.14 (1H, s). |

TABLE 1-2-continued

| No. | R | R' | D |
|---|---|---|---|
| 52 | (indole, 7-substituted) | (propanoyl-thiazol-2-yl) | MS: 462 (M + H)+, N1: 0.30-3.40 (13H, m), 3.77 (1H, d, J = 16.2 Hz), 3.89 (1H, d, J = 16.2 Hz), 3.95-4.10 (1H, m), 6.04 (1H, s), 6.46-7.54 (5H, m), 6.69 (1H, s), 6.78 (1H, s), 7.58 (1H, d, J = 3.3 Hz), 7.75 (1H, d, J = 3.3 Hz), 10.60 (1H, s). |
| 53 | (quinolin-8-yl) | (propanoyl-thiazol-2-yl) | MS: 474 (M + H)+, N1: 0.30-3.40 (13H, m), 3.80 (1H, d, J = 16.5 Hz), 3.88 (1H, d, J = 16.5 Hz), 4.00-4.15 (1H, m), 6.71 (1H, s), 6.74 (1H, s), 6.76 (1H, s), 7.48-8.85 (3H, m), 7.54 (1H, d, J = 3.3 Hz), 7.70 (1H, d, J = 3.3 Hz), 7.94 (1H, dd, J = 1.8, 7.8 Hz), 8.88 (1H, dd, J = 1.8, 8.4 Hz) |
| 54 | (benzothiophen-3-yl) | (propanoyl-pyridin-2-yl) | MS: 473 (M + H)+, N1: 0.30-3.40 (13H, m), 3.78 (1H, d, J = 16.5 Hz), 3.84 (1H, d, J = 16.5 Hz), 3.91-4.05 (1H, m), 5.96 (1H, s), 6.72 (1H, s), 6.80 (1H, s), 7.15-7.46 (5H, m), 7.62-8.04 (3H, m), 8.46-8.54 (1H, m) |
| 55 | (benzothiophen-7-yl) | (propanoyl-pyridin-2-yl) | MS: 473 (M + H)+, N1: 0.35-3.10 (13H, m), 3.81 (1H, d, J = 16.5 Hz), 3.91 (1H, d, J = 16.5 Hz), 3.90-4.05 (1H, m), 5.90 (1H, s), 6.81 (1H, s), 6.84 (1H, s), 7.00-7.90 (8H, m), 8.45-8.50 (1H, m) |

Example 56

(Process 1)

A hydrazine hydrate (0.96 mL, excess) was added to a methanol solution (6.5 mL) of a compound (277 mg, 0.649 mmol) of the following structural formula (XI) described in WO02/44180, and stirred at 50° C. for 26 hours. The solvent was removed under reduced pressure to obtain a crude hydrazide. An acetic anhydride (332 mg, 3.25 mmol) was added to a pyridine solution (6.5 mL) of the crude hydrazide at 0° C. and stirred for 2 hours. The solvent was removed under reduced pressure, and the residue was treated with a silica gel column chromatography to obtain a Process 1 compound from fractions of methanol:methylene chloride (1:4).

1H-NMR (300 MHz, DMSO-d6) δ=0.50-3.40 (13H, m), 1.84 (3H, s), 3.72-3.90 (5H, m), 3.96 (1H, m), 5.82 (1H, brs), 6.66 (1H, brs), 6.73 (1H, brs), 6.86-7.35 (4H, m), 9.73 (2H, brs)

MS(ESI) m/z 470 (M+H)+, 468 (M−H)−

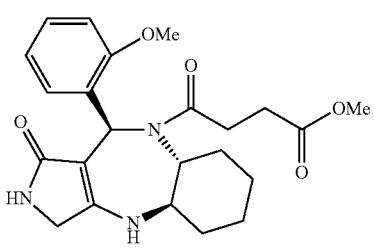

(XI)

(Process 2)

A phosphorous oxychloride (0.13 mL, 1.40 mmol) was added to a dioxane solution (14 mL) of the Process 1 compound (132 mg, 0.281 mmol), and stirred at 90° C. for 1 hour. The reaction solution was cooled down to 0° C., an aqueous solution of 1N sodium hydroxide was added thereto and neutralized. Then, the reaction solution was extracted with an ethyl acetate. The organic layer thereof was washed with a saturated saline solution, dried on a magnesium sulfate, and the solvent thereof was removed under reduced pressure. The solvent was removed under reduced pressure, and the residue was purified with a thin layer silica gel column chromatography (methanol:methylene chloride=1:5) to obtain a compound 56 (32 mg, 25%).

Example 57

A compound 57 was obtained by the same method as that of Example 56.

Example 58

A diphosphorus pentasulfide (204 mg, 0.922 mmol) was added to a dioxane solution (7.4 mL) of the Process 1 compound (173 mg, 0.369 mmol) of Example 56, and stirred at 90° C. for 3.5 hours. The reaction solution was cooled down to room temperature, and the solvent was removed under reduced pressure. The residue was purified with a thin layer silica gel column chromatography (methanol:methylene chloride=1:5) to obtain a compound 58 (27 mg, 16%).

Example 59

A compound 59 was obtained by the same method as that of Example 58.

Example 60

(Process 1)
A dichloromethane solution (2 mL) of a chloroacetic anhydride (164 mg, 0.958 mmol) was added at 0° C. to a suspension consisting of a compound (200 mg, 0.639 mmol) of the following structural formula (XII) described in WO02/44180, dichloromethane (15 mL) and pyridine (0.15 mL, 1.92 mmol), and stirred at room temperature for 15 hours. The reaction solution was concentrated and azeotroped with toluene. Then, the solution was dissolved in dichloromethane and washed with 0.1N hydrochloric acid and a saturated saline solution, respectively. The organic layer thereof was dried on an anhydrous sodium sulfate, concentrated, and then purified with a silica gel column chromatography (methanol:dichloromethane=1:19 to 1:3) to obtain a Process 1 compound (162 mg, 65%) as a white solid substance.

1H-NMR (300 MHz, DMSO-d6) δ=0.50-3.40 (9H, m), 3.59 (1H, d, J=12.9 Hz), 3.72 (1H, d, J=12.9 Hz), 5.09 (1H, d, J=10.8 Hz), 5.15 (1H, d, J=10.8 Hz), 5.61 (1H, brs), 6.68 (1H, brs), 6.71 (1H, brs), 6.87-6.96 (1H, m), 7.00-7.07 (1H, m), 7.10-7.18 (1H, m), 7.26-7.46 (6H, m)

MS(ESI) m/z 466 (MH+), 464 (M–H)–

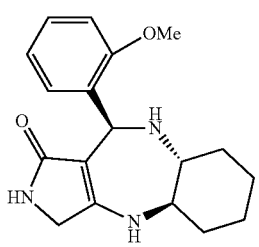

(XII)

(Process 2)
A potassium carbonate (88.0 mg, 0.640 mmol) was added to a N,N-dimethylformamide solution (1 mL) of 2-hydroxypyridine (61.0 mg, 0.640 mmol), and stirred for 5 minutes. Then, the compound (50.0 mg, 0.128 mmol) obtained in Process 1 was added thereto and stirred at 90° C. for 15 hours. The reaction solution was separated with ethyl acetate-water, and extracted with dichloromethane from the water layer thereof. The organic layer thereof was combined together, washed with a saturated saline solution, and then dried on an anhydrous sodium sulfate. The residue obtained by concentration was purified with a thin layer chromatography (methanol:ethyl acetate=1:4) to obtain a compound 60 (29.3 mg, 51%).

Examples 61 and 63

Compounds 61 and 63 were obtained by the same method as that of Example 60.

Example 62

A compound 62 was synthesized in accordance with the method described in WO02/44180.

Example 64

(Process 1)
A malonic monoethyl ester (361 mg, 2.73 mmol) and WSC/HCl (393 mg, 2.05 mmol) were added to a N,N-dimethylformamide solution (6.8 mL) of the compound (XII) (214 mg, 0.684 mmol) in Process 1 of Example 60, and stirred at room temperature for 23 hours. After removing the solvent under reduced pressure, the reaction solution was separated with ethyl acetate-water. Then, the organic layer thereof was washed with an aqueous solution of a saturated sodium hydrogen carbonate and a saturated saline solution, respectively. After being dried on an anhydrous magnesium sulfate, the solvent was removed under reduced pressure to obtain a crude acyl compound (a mixture with a diacyl compound).

A 28% ammonia water (7.5 mL) was added to an ethanol solution (7.5 mL) of the crude acyl compound, and stirred at 50° C. for 72 hours. After being cooled down to room temperature, 6N—HCl was added and neutralized. Then, the solvent was removed under reduced pressure. Methanol was added to the residue, and insoluble substance was filtered out. The solvent was removed under reduced pressure, and the residue was purified with a silica gel column chromatography (methanol:methylene chloride=1:4) to obtain a Process 1 compound (195 mg, 72%).

1H-NMR (300 MHz, DMSO-d6) δ=0.50-3.60 (11H, m), 3.73 (1H, d, J=16.7 Hz), 3.83 (1H, d, J=16.7 Hz), 3.85 (3H, s), 4.01 (1H, m), 5.67 (1H, br s), 6.86-7.57 (8H, m)

MS(ESI) m/z 399 (M+H)+, 397 (M–H)–

(Process 2)
A diphosphorus pentasulfide (204 mg, 0.920 mmol) was added to a 1,2-dimethoxyethane solution (12 mL) of the Process 1 compound (183 mg, 0.460 mmol), and stirred at 50° C. for 30 minutes. After the solvent was removed under reduced pressure, the residue was purified with a thin layer silica gel column chromatography (methanol:methylene chloride=1:8) to obtain a Process 2 compound (26 mg, 14%).

1H-NMR (300 MHz, DMSO-d6) δ=0.50-3.40 (9H, m), 3.72 (1H, d, J=15.8 Hz), 3.76 (1H, d, J=14.9 Hz), 3.83 (1H, d, J=14.9 Hz), 3.90 (3H, s), 4.02 (1H, m), 4.15 (1H, d, 15.8 Hz), 5.67 (1H, br s), 6.70 (2H, d, J=11.7 Hz), 6.86-7.35 (4H, m), 9.25 (1H, br s), 9.56 (1H, br s)

MS(ESI) m/z 414 (M+H)+, 412 (M–H)–

(Process 3)

An aqueous solution of 40% chloroacetaldehyde (52 mg, 0.266 mmol) was added to a N,N-dimethylformamide solution (2 mL) of the Process 2 compound (22 mg, 0.053 mmol), and stirred at 50° C. for 3 hours. After the reaction solution was cooled down to room temperature, PS-TsNHNH2 (220 mg, 0.532 mmol) was added thereto and stirred at room temperature for 3.5 hours. Then, a resin was filtered out (and thoroughly washed with methylene chloride), and the solvent was removed under reduced pressure. The residue was purified with a thin layer silica gel column chromatography (methanol:methylene chloride=1:10) to obtain a compound 64 (9 mg, 39%).

The structural formulae of Compounds 56 to 64 and data on the compounds are shown in the following Table 2. In this regard, the symbols in the Table are as follows: No.: Example No., R: a substituent on a benzene ring, R': an acyl group, D: data on the compound, MS:ESI-MS m/z, N1: 1H-NMR (DMSO-d6, TMS internal standard, δ ppm). The number located in front of a substituent in R indicates the position of the substituent on a benzene ring.

TABLE 2

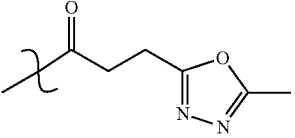

| No. | R | R' | D |
|---|---|---|---|
| 56 | 2-OMe | 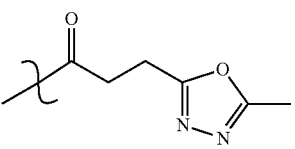 | N1: 0.50-3.40 (13H, m), 2.43 (3H, s), 3.70-4.03 (6H, m), 5.81 (1H, brs), 6.67 (1H, brs), 6.73 (1H, brs), 6.86-7.36 (4H, m) MS: 452 (M + H)+, 450 (M − H)− |
| 57 | 2-OCF3 | 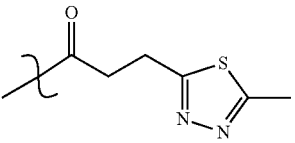 | N1: 0.50-3.40 (13H, m), 2.41 (3H, s), 3.70-4.03 (3H, m), 5.83 (1H, brs), 6.83 (2H, brs), 7.18-7.52 (4H, m) MS: 506 (M + H)+, 504 (M − H)− |
| 58 | 2-OMe | 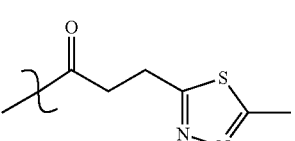 | N1: 0.50-3.40 (13H, m), 2.66 (3H, s), 3.72 (3H, s), 3.75-3.88 (2H, m), 3.99 (1H, m), 5.80 (1H, brs), 6.70 (1H, brs), 6.74 (1H, brs), 6.82-7.39 (4H, m) MS: 468 (M + H)+, 466 (M − H)− |
| 59 | 2-OCF3 | | N1: 0.50-3.40 (13H, m), 2.50 (3H, s), 3.70-4.12 (3H, m), 5.83 (1H, brs), 6.85 (2H, brs), 7.20-7.55 (4H, m) MS: 522 (M + H)+, 520 (M − H)− |
| 60 | 2-OMe | 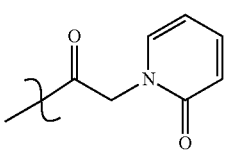 | N1: 0.50-3.40 (9H, m), 3.78 (1H, J = 16.0 Hz, d), 3.83 (1H, J = 16.0 Hz, d), 3.80-3.98 (1H, m), 3.95 (3H, s), 4.63 (1H, J = 15.6 Hz, d), 5.38 (1H, J = 15.6 Hz, d), 5.76 (1H, s), 6.10-6.40 (2H, m), 6.69 (1H, s), 6.76 (1H, s), 6.86-7.10 (3H, m), 7.27-7.52 (3H, m) MS: 449 (M + H)+ |
| 61 | 2-OMe | 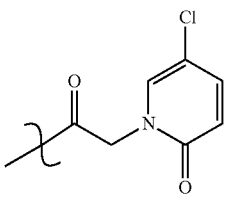 | N1: 0.50-3.40 (9H, m), 3.75 (1H, J = 16.0 Hz, d), 3.84 (1H, J = 16.0 Hz, d), 3.80-3.97 (1H, m), 3.95 (3H, s), 4.60 (1H, J = 15.3 Hz, d), 5.44 (1H, J = 15.3 Hz, d), 5.72 (1H, s), 6.40 (1H, J = 9.9 Hz, d), 6.69 (1H, s), 6.76 (1H, s), 6.86-7.37 (4H, m), 7.48 (1H, J = 15.3 & 3.0 Hz, dd), 7.82 (1H, J = 3.0 Hz, d) MS: 483 (M + H)+ |

TABLE 2-continued

| No. | R | R' | D |
|---|---|---|---|
| 62 | 2-OMe | (acyl group with pyridinone-CF₃) | N1: 0.50-3.40 (10H, m), 3.72 (1H, d, J = 16.5 Hz), 3.77 (3H, s), 3.81 (1H, d, J = 16.5 Hz), 3.90-4.05 (1H, m), 4.00-4.15 (2H, m), 5.69 (1H, s), 6.53 (1H, d, J = 6.9 Hz), 6.66 (1H, s), 6.71 (1H, s), 6.89 (1H, d, J = 6.6 Hz), 6.94-7.30 (4H, m), 7.64 (1H, d, J = 9.6 Hz), 8.40 (1H, s). MS: 529 (M − H)−. |
| 63 | 2-OMe | (acyl group with pyridyloxy) | N1: 0.50-3.40 (9H, m), 3.71 (1H, J = 16.0 Hz, d), 3.81 (1H, J = 16.0 Hz, d), 3.87 (3H, s), 3.70-3.98 (1H, m), 4.94 (1H, J = 15.0 Hz, d), 5.15 (1H, J = 15.0 Hz, d), 5.73 (1H, s), 6.70 (1H, s), 6.76 (1H, s), 6.88-7.38 (6H, m), 8.12-8.20 (2H, m) MS: 449 (M + H)+, 447 (M − H)− |
| 64 | 2-OMe | (acyl group with thiazole) | N1: 0.50-3.40 (9H, m), 3.73 (1H, d, J = 16.2 Hz), 3.80 (1H, d, J = 16.2 Hz), 3.85 (3H, s), 4.01 (1H, m), 4.20 (1H, d, J = 16.8 Hz), 4.51 (1H, d, J = 16.8 Hz), 5.89 (1H, br s), 6.71 (2H, d, J = 4.8 Hz), 6.86-7.38 (4H, m), 7.64 (1H, d, J = 3.0 Hz), 7.70 (1H, d, J = 3.0 Hz) MS: 439 (M + H)+, 437 (M − H)− |

Example 65

(Evaluation of the Sugar Transporting Capacity)

1. Preparation of Adipose Cells of Rats:

After the decapitation and venesection of 6 male Wistar rats (body weight: 150 to 200 g), an incision was made in the abdomen of each rat to extract 6 g in total of epididymal adipose tissues. The tissues were finely cut into 2 mm×2 mm pieces in 6 ml of KRH (Krebs-Ringer Hepes, composition: 130 mM of sodium chloride, 4.7 mM of potassium chloride, 1.2 mM of potassium dihydrogenphosphate, 1.2 mM of magnesium sulfate, 1 mM of calcium chloride and 25 mM of Hepes, pH=7.6) containing 5% of BSA (bovine serum albumin). 24 mg of collagenase (type I) was added thereto and the digestion treatment was conducted for about 40 minutes to obtain about 6 ml of isolated adipose cells. The collagenase was removed by the buffer exchange. 2% BSA/KRH solution was added to the residue for the re-suspension to obtain 45 ml of an adipose cell suspension.

2. Evaluation of the Sugar Transporting Capacity:

The sugar transporting capacity of the compound of the present invention was evaluated with reference to a method described in a literature [Annual Review of Biochemistry, Vol. 55, p. 1059 (1986)]. In the test, 200 μL of the adipose cell suspension was poured in each polystyrene test tube, 100 μL of the solution of the test substance (by dilution of 10 mg/mL dimethyl sulfoxide solution with KRH) was added thereto, and the obtained mixture was shaken and then cultured at 37° C. for 30 minutes.

The sugar transporting capacity was evaluated by measuring the quantity of 2-[$^{14}$C(U)]-deoxy-D-glucose incorporated per a unit time. Namely, 2-[$^{14}$C(U)]-deoxy-D-glucose was added to the adipose cell suspension after the pre-culture (the final concentration: 0.5 μCi/sample). 5 minutes later, cytochalasin B (final concentration: 10 μM) was added to the mixture to terminate the sugar transportation. After forming a dinonyl phthalate layer, the obtained mixture was centrifuged to separate the adipose cells from the buffer. The quantity of 2-[$^{14}$C(U)]-deoxy-D-glucose contained in the adipose cell layer was determined with a liquid scintillation counter to determine the quantity of the incorporated sugar. In this evaluation system, when insulin (100 nM) having the effect of increasing the sugar-transporting capacity was used, the effect was about 7 times as high as that obtained in the insulin-free control group.

The results of the evaluation of the sugar-transporting capacity obtained by using the compounds of the present invention are shown in Table 3. The sugar-transporting capacity in Table 3 was determined in terms of the concentration (EC$_{50}$: μg/mL) of a test compound, having a reinforcing effect corresponding to 50% on the basis of the reinforcing effect of insulin (100 nM). (The symbols in Table 3 are as follows: No: Example No., and A: sugar-transporting capacity.)

TABLE 3

| No. | A |
|---|---|
| 14 | 0.0060 |
| 20 | 0.064 |
| 22 | 0.090 |
| 25 | 0.020 |
| 27 | 0.050 |
| 33 | 0.10 |
| 34 | 0.070 |
| 38 | 0.021 |
| 41 | 0.10 |
| 42 | 0.060 |
| 43 | 0.070 |
| 44 | 0.060 |

TABLE 3-continued

| No. | A |
|---|---|
| 46 | 0.040 |
| 52 | 0.040 |
| 55 | 0.0040 |

What is claimed is:

1. A compound or pharmaceutically acceptable salt, which is selected from the group consisting of:

(a) a compound of formula:

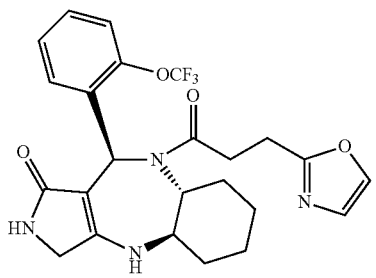

(b) a pharmaceutically acceptable salt of a compound of formula:

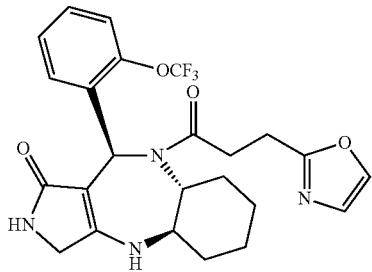

(c) a compound of formula:

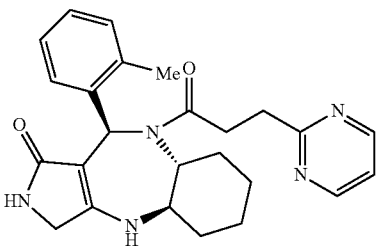

(d) a pharmaceutically acceptable salt of a compound of formula:

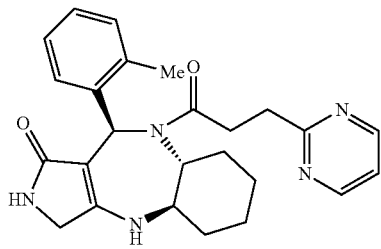

(e) a compound of formula:

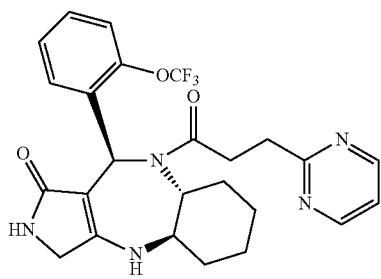

and (f) a pharmaceutically acceptable salt of a compound of formula:

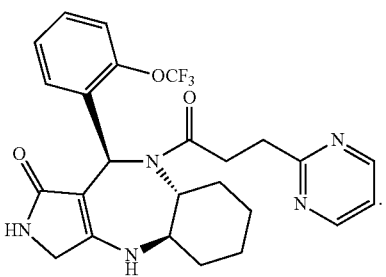

2. A fused polycyclic compound or pharmaceutically acceptable salt thereof according to claim 1, which is a fused polycyclic compound of formula:

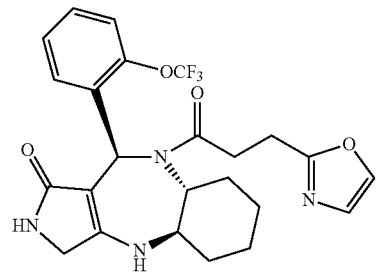

or a pharmaceutically acceptable salt thereof.

3. A fused polycyclic compound or pharmaceutically acceptable salt thereof according to claim 1, which is a fused polycyclic compound of formula:

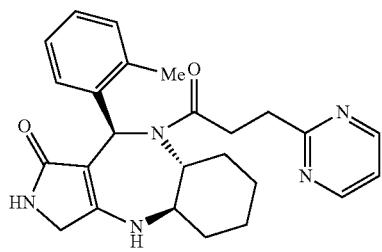

or a pharmaceutically acceptable salt thereof.

4. A fused polycyclic compound or pharmaceutically acceptable salt thereof according to claim 1, which is a fused polycyclic compound of formula:

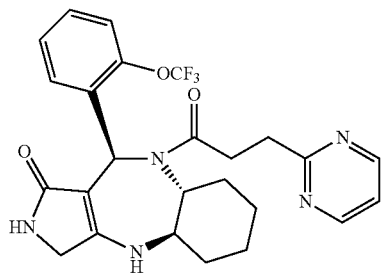

or a pharmaceutically acceptable salt thereof.

5. A method for increasing the sugar-transporting capacity, comprising administering an effective amount of a fused polycyclic compound or pharmaceutically acceptable salt thereof according to claim 2 to a subject in need thereof.

6. A method for treating hypoglycemia, comprising administering an effective amount of a fused polycyclic compound or pharmaceutically acceptable salt thereof according to claim 2 to a subject in need thereof.

7. A method for treating diabetes, diabetic peripheral neuropathy, diabetic nephropathy, diabetic retinopathy, diabetic macroangiopathy, impaired glucose tolerance, or obesity, comprising administering an effective amount of a fused polycyclic compound or pharmaceutically acceptable salt thereof according to claim 2 to a subject in need thereof.

8. A pharmaceutical composition which comprises a fused polycyclic compound or pharmaceutically acceptable salt thereof according to claim 2 and a pharmaceutically acceptable carrier.

9. A method for increasing the sugar-transporting capacity, comprising administering an effective amount of a compound or pharmaceutically acceptable salt according to claim 1 to a subject in need thereof.

10. A method for treating hypoglycemia, comprising administering an effective amount of a compound or pharmaceutically acceptable salt according to claim 1 to a subject in need thereof.

11. A method for treating diabetes, diabetic peripheral neuropathy, diabetic nephropathy, diabetic retinopathy, diabetic macroangiopathy, impaired glucose tolerance, or obesity, comprising administering an effective amount of a compound or pharmaceutically acceptable salt according to claim 1 to a subject in need thereof.

12. A pharmaceutical composition, which comprises a fused polycyclic compound or pharmaceutically acceptable salt thereof according to claim 1 and a pharmaceutically acceptable carrier.

13. A method for increasing the sugar-transporting capacity, comprising administering an effective amount of a compound or pharmaceutically acceptable salt according to claim 3 to a subject in need thereof.

14. A method for treating hypoglycemia, comprising administering an effective amount of a compound or pharmaceutically acceptable salt according to claim 3 to a subject in need thereof.

15. A method for treating diabetes, diabetic peripheral neuropathy, diabetic nephropathy, diabetic retinopathy, diabetic macroangiopathy, impaired glucose tolerance, or obesity, comprising administering an effective amount of a compound or pharmaceutically acceptable salt according to claim 3 to a subject in need thereof.

16. A pharmaceutical composition, which comprises a fused polycyclic compound or pharmaceutically acceptable salt thereof according to claim 3 and a pharmaceutically acceptable carrier.

17. A method for increasing the sugar-transporting capacity, comprising administering an effective amount of a compound or pharmaceutically acceptable salt according to claim 4 to a subject in need thereof.

18. A method for treating hypoglycemia, comprising administering an effective amount of a compound or pharmaceutically acceptable salt according to claim 4 to a subject in need thereof.

19. A method for treating diabetes, diabetic peripheral neuropathy, diabetic nephropathy, diabetic retinopathy, diabetic macroangiopathy, impaired glucose tolerance, or obesity, comprising administering an effective amount of a compound or pharmaceutically acceptable salt according to claim 4 to a subject in need thereof.

20. A pharmaceutical composition, which comprises a fused polycyclic compound or pharmaceutically acceptable salt thereof according to claim 4 and a pharmaceutically acceptable carrier.

* * * * *